United States Patent [19]

Ponting

[11] Patent Number: 5,405,772
[45] Date of Patent: Apr. 11, 1995

[54] MEDIUM FOR LONG-TERM PROLIFERATION AND DEVELOPMENT OF CELLS

[75] Inventor: Ian L. O. Ponting, Woodland Hills, Calif.

[73] Assignee: Amgen Inc., Thousand Oaks, Calif.

[21] Appl. No.: 79,719

[22] Filed: Jun. 18, 1993

[51] Int. Cl.$^6$ ............................................. C12N 5/00
[52] U.S. Cl. ............................. 435/240.31; 435/240.3
[58] Field of Search ........................... 435/240.3, 240.31

[56] References Cited

U.S. PATENT DOCUMENTS

| | | | |
|---|---|---|---|
| 4,443,546 | 4/1984 | Stemerman et al. | 435/240 |
| 4,533,637 | 8/1985 | Yamane et al. | 435/240 |
| 4,560,655 | 12/1985 | Baker | 435/241 |
| 4,786,599 | 11/1988 | Cheesebeuf et al. | 435/240.31 |
| 4,816,401 | 3/1989 | Taupier et al. | 435/240.31 |
| 4,940,666 | 7/1990 | Boyce et al. | 435/240.2 |
| 5,030,105 | 7/1991 | Kuri-Harcuch et al. | 435/29 |
| 5,045,454 | 9/1991 | Bertheussen | 435/29 |
| 5,122,469 | 6/1992 | Mather et al. | 435/240.2 |
| 5,132,223 | 7/1992 | Levine et al. | 435/240.2 |
| 5,135,866 | 8/1992 | Heifetz et al. | 435/240.31 |
| 5,143,842 | 9/1992 | Ham et al. | 435/240.2 |
| 5,147,790 | 9/1992 | Wilson | 435/70.3 |
| 5,232,848 | 8/1993 | Wolfe et al. | 435/240.31 |
| 5,326,699 | 7/1994 | Torishima | 435/240.2 |
| 5,328,844 | 7/1994 | Moore | 435/240.31 |

FOREIGN PATENT DOCUMENTS

WO91/18620  12/1991  WIPO.
WO92/18615  10/1992  WIPO.
WO93/09220  5/1993  WIPO.

OTHER PUBLICATIONS

Brown, R. L., et al., "J. of Cellular Phys.," vol. 115, 1983, pp. 191–198.

Flesch, I., et al., "Immunobiol. (Stuttgart)," vol. 171 (1–2), 1986, pp. 14–26.

K. Koneshina, "J. Tokyo Med. 611," vol. 42 (6), 1984, pp. 1031–1041–Translation.

H. Hoshi, et al., "Kosonkinbyo Kenkyu Zasshi," vol. 34 (1–3), 1982, pp. 14–27. Translation.

Barnes, D. & Sato, G., Serum–free cell culture: A Unifying approach. Cell. 1980; 22:649–655.

Cormier, F., Ponting, I. L. O., Heyworth, C. M. & Dexter, T. M., Serum–free culture of enriched murine haemopoietic stem cells 1: Growth Factors. 1991; 4:157–164.

Dainiak, N., Role of defined and undefined serum additives to hematopoietic stem cell culture. Hematopoietic Stem Cell Physiology. New York: Alan R. Liss; 1985:59–76.

Deslex, S., Negrel, R. & Aihaud, G. Development of a chemically defined serum–free medium for differentiation of rat adipose. Experimental Cell Research. 1987; 168:15–30.

Dexter, T. M., Allen, T. D. & Lajtha, L. G. Conditions controlling the proliferation of haemopoietic stem cells in vitro. Journal of Cellular Physiology. 1977; 91:335–344.

(List continued on next page.)

*Primary Examiner*—Douglas W. Robinson
*Assistant Examiner*—Kristin Larson
*Attorney, Agent, or Firm*—Robert R. Cook

[57] ABSTRACT

A serum-free or serum-depleted medium for the short- and long-term proliferation and development of cells, particularly hematopoietic cells and bone marrow stromal cells, the medium comprising cell proliferation and development effective amounts of:
  a standard culture medium such as Iscove's modified Dulbecco's medium; serum albumin; transferrin; a source of lipids and fatty acids; cholesterol; a reducing agent; pyruvate; a glucocorticoid (when the cells to be cultured are hematopoietic cells); nucleosides for synthesis of DNA and RNA; growth factors that stimulate the proliferation and development of stromal cells and cells from a variety of tissues or organs, such as epidermal growth factor, fibroblast growth factor, platelet derived growth factor, and insulin; and extracellular matrix materials, such as collagen, fibronectin, and laminin.

16 Claims, 8 Drawing Sheets

OTHER PUBLICATIONS

Dexter, T. M., Spooncer, E., Simmons, P. & Allen, T. D. Long-term marrow culture: New York: Alan R. Liss: 57–95 1984.

Dorshkind, K. In vitro differentiation of B lymphocytes from primitive hemopoietic precursors present in long-term bone marrow cultures. The Journal of Immunology. 1985; 136(2): 422–427.

Dorshkind, K. Regulation of hemopoiesis by bone marrow stromal cells and their products. Annual Review of Immunology. 1990; 8: 111–137.

Drouet, X., Douay, L., Giarratana, M. C., Baillou, C. L., Gorin, N. C., Salmon, C. & Najman, A. Human liquid bone marrow culture in serum-free medium. British Journal of Haematology. 1989; 73: 143–147.

Greenberger, J. S. Long-term hematopoietic cultures. In: Methods in Hematology. Golde ed.; 1985: 203–242.

Greenberger, J. S., Sensitivity of corticosteroid-dependent, insulin-resistant liopgenesis in marrow preadipocytes of diabetic-obese mice. Nature. 1978; 275: 752–754.

Kumar, R. K., O'Grady, R., Li, W., Smith, L. W., Rhodes, G. C. Primary culture of adult mouse lung fibroblasts in serum-free medium: responses to growth factors. Experimental Cell Research. 1991; 193: 398–404.

Migliaccio, G. Migliaccio, A. R. & Adamson, J. W. The biology of hematopoietic growth factors: Studies in vitro under serum-deprived conditions. Experimental Hematology. 1990; 18: 1049–1055.

Migliaccio, G. & Migliaccio, A. R. Cloning of human erythroid progenitors (BFU-E) in the absence of fetal bovine serum. Br. J. Haematol. 1987; 67: 129–133.

Ponting, I. L. O., Heyworth, C. M., Cormier, F. & Dexter, T. M. Serum-free culture of enriched murine haemopoietic stem cells II: Effects of growth factors and haemin on development. Growth Factors. 1991; 4: 165–173.

Whitlock, C. A., & White, O. N. Long-term culture of B lymphocytes and their precursors from murine bone marrow. Proceedings of the National Academy of Science. 1982; 79: 3608–3612.

Whitlock, C. A., et al., Murine B cell lymphopoiesis in long term culture. Journal of Immunological Methods. 1984; 67: 353–369.

Koller, M. R. et al., Expansion of Primitive Human Hematopoietic Progenitors in a Perfusion Bioreactor System with IL-3, IL-6, and Stem Cell Factor. In: Bio/Technology vol. 11; Mar. 1993: 358–363.

Brandt, J. et al., Cytokine-dependent Long-Term Culture of Highly Enriched Precursors of Hematopoietic Progenitor Cells from Human Bone Marrow. Journal of Clinical Investigation, vol. 86, Sep. 1990, 932–941.

Teofili, L. et al. Effects of a preformed extracellular matrix on long-term serum-free bone marrow culture. Ann Hematol (1992) 65: 22–25.

Lipson, S. M., "Diagn. Microbiol. Infect. Dis.," vol. 4, #3 Mar. 1986, pp. 203–214.

Vincent, F., et al., "Exp. Hematol.," vol. 20, #1, Jan. 1992, pp. 17–23.

Sigma Cell Culture Reagents 1992 Catalogue/Price List, pp. 20, 60–61, 67–70, 77.

Gibco BRL Catalogue Reference Guide, 1990, p. 27, 195.100.

Schlaego, E. J., et al., "J. of Immunological Methods", vol. 143 (1), 1992, pp. 111–120.

Lipson, S. M., et al., "Abstracts of the Annual Meeting of the ASM," vol. 84 (0), 1984, #E52.

Uittenbogaart, C. H., et al., "In vitro," vol. 19 (1), Jan. 1983, pp. 67–72.

FIG.8

| MOUSE STRAIN | TREATMENT | HEMATOPOIETIC CELL MORPHOLOGY (%) | | | |
|---|---|---|---|---|---|
| | | NEUTROPHILS | B CELLS | MAST CELLS | MACROPHAGES |
| +/+ | +HC | 96 | 0 | 0 | 4 |
| +/+ | -HC | 0 | 0 | 0 | 100 |
| OP/OP | -HC | 80 | 17 | 3 | 0 |
| OP/OP | -HC+SCF+IL-7 | 35 | 31 | 34 | 0 |

+HC = hydrocortisone present
-HC = hydrocortisone absent
+SCF = stem cell factor present
+IL-7 = interleukin-7 present

MEDIUM FOR LONG-TERM PROLIFERATION AND DEVELOPMENT OF CELLS

BACKGROUND OF THE INVENTION

I. Field of the Invention

This invention relates to serum-free or serum-depleted culture media for supporting the proliferation and development of cells. More particularly, it is directed to culture media for the long-term growth of hematopoietic cells and the stromal cells which support their growth. It is also directed to methods for culturing mammalian cells from different tissues and organs using such media. The media and methods enable the maintenance of cell growth and development for up to several months.

II. Description of Background and Related Art

One aspect of the present invention is a medium for culturing cells, particularly mammalian cells in the absence of or substantial depletion of serum, whereby the medium is chemically well defined, while still providing long-term support of development and proliferation of such cells.

In the past, many types of mammalian cells have been isolated and attempts have been made to propagate the cells in culture for further study or use. The media used for such culture have typically included sources of nutrients, adhesion factors and growth factors required for cell proliferation and development, many provided by horse, bovine or calf serum. However, the use of serum to support cell culture has been problematic since it does not provide physiological conditions. Indeed, the only time a cell would see the sort of serum concentration normally used for cell culture would be at the site of a wound, where the blood is clotting. The use of serum is further complicated by high cost and the presence of undefined components in the serum which may vary from sample to sample. The presence or absence of these undefined components has led to inconsistent results in the culture of cells and lack of control over the culturing process. For example, a particular serum sample may introduce particular components into the culture medium that inhibit the growth of the cells.

In response to problems associated with the presence of serum, a variety of serum-free media have been produced in the past. See for example:

1) Barnes, D. & Sato, G. Serum- free cell culture. A unifying approach. Cell. 1980; 22: 649;
2) Cormier, F., Ponting, I. L. O., Heyworth, C. M. & Dexter, T. M. Serum-free culture of enriched murine haemopoietic stem cells I: Effect of haemopoietic growth factors on proliferation. Growth Factors. 1991; 4: 157–164;
3) Deslex, S., Negrel, R. & Ailhaud, G. Development of a chemically defined serum-free medium for differentiation of rat adipose precursor cells. Experimental Cell Research. 1987; 168: 15–30;
4) Drouet, X., Douay, L., Giarratana, M. C., Baillou, C. L. Gorin, N. C., Salmon, C. H. & Najman, A. Human long-term bone marrow culture in serum-free medium. British Journal of Haematology. 1989; 73: 143–147;
5) Kumar, R. K., O'Grady, R., Li, W., Smith, L. W., Rhodes, G. C. Primary culture of adult mouse lung fibroblasts in serum-free medium: responses to growth factors. Experimental Cell Research. 1991; 193:398–404;
6) Migliaccio, G. Migliaccio, A. R. & Adamson, J. W. The biology of hematopoietic growth factors: Studies in vitro under serum-deprived conditions. Experimental Hematology 1990; 18: 1049–1055; and
7) Ponting, I. L. O., Heyworth, C. M., Cormier, F. & Dexter, T. M. Serum-free culture of enriched murine haemopoietic stem cells II: Effects of growth factors and haemin on development. Growth Factors. 1991; 4: 165–173.

As described in a number of the cited articles, there already exist methods for the short-term (up to 3–4 weeks) serum-free culture of hematopoietic progenitor cells, using added hematopoietic growth factors as the proliferative and developmental stimuli. However, the development of ideal serum-free media to study the long-term culture of hematopoietic cells has proven to be particularly difficult.

Prior to the invention described herein, mammalian long-term hematopoiesis has been studied in vitro mainly using serum supplemented bone marrow culture systems which appear to closely mimic some of the processes that occur in vivo. The first of these was described by Dexter, T. M., et al, J. Cell. Physiol., 91: 335–344 (1977) and involves the formation of an adherent layer of murine bone marrow stromal cells, which included endothelial cells, fibroblasts, adipocytes and macrophages. This cell layer was required to support the hematopoietic cells, probably by providing a physical adhesive matrix as well as the correct cell to cell signalling, including the necessary growth factors for hematopoietic cell proliferation and development.

The hematopoiesis which takes place in these Dexter cultures occurs in intimate contact with the stromal cell layer. In many cases the stem cells and progenitor cells proliferate under the stromal cells forming foci called cobblestone regions due to their characteristic appearance under phase microscopy. As the hematopoietic cells mature, many of them migrate to the uppermost surface of the stromal cells. Further maturation to a fully differentiated state results in release of the hematopoietic cells into the surrounding medium where they are removed by the bi-weekly feeding.

This culture system enabled the maintenance of hematopoiesis for several months, with the constant production of progenitor cells. Soon after, a similar system was developed for human cells (Gartner, S. and Kaplan, H. S., Proc. Natl. Acad. Sci. USA, 77: 4756–4759 (1980)).

One important drawback of the Dexter method was that it mainly allowed the development of macrophages and neutrophils, at the expense of other cell types normally produced by the bone marrow, particularly B lymphocytes. A method for the long-term production of B lymphocytes was discovered by Whitlock, C. A. and Witte, O. N., Proc. Natl. Acad. Sci. USA 79: 3608–3612 (1982). This system differed from that described by Dexter, et al. in that the horse serum was replaced with fetal calf serum and hydrocortisone was replaced with 2-mercaptoethanol. However, this system precluded the development of hematopoietic lineages other than B lymphocytes. The reason(s) for the differences in the development that occurs in these two culture systems, and why they do not mimic all aspects of bone marrow hematopoiesis, is unknown but is possibly a reflection of the use of serum.

In spite of the many attempts that have been made to produce an ideal, chemically controlled medium for culturing cells, especially mammalian hematopoietic cells, a number of shortcomings have persisted in such media. For example, prior media do not truly enable long-term culture of such cells. In accordance with the present invention, "long-term" is defined as greater than or equal to approximately eight weeks of continuous proliferation and development, including generation of new progenitor cells in the medium. The media of the present invention can produce up to three to five months of continuous growth and development in culture. There have been no prior serum-free media that have been able to achieve such long-term culture of mammalian hematopoietic cells.

The following is a brief description of some of the additional related prior art:

Cormier, et al. Growth Factors. 1991; 4: 157–164, relates to serum-free culture of enriched murine hematopoietic stem cells and focuses on the effect of certain growth factors on proliferation. However, the medium disclosed in this publication contains different components in different relative proportions as compared to the present invention, and was unable to achieve any long-term growth (as defined herein), in contrast to the present media.

Dexter, T. M., et al., J. Cell. Physiol. 91: 335–344 (1977), discloses the classical Dexter long-term bone marrow culture method. It is notable that this method contains serum, unlike the present invention. As a result its use is restricted to certain mouse strains and even with such strains the growth is not as pronounced as in the current invention.

Dexter, T. M., et al., Long-Term Bone Marrow Culture. New York: Alan R. Liss: 57–96, is a review of long-term marrow culture techniques and media. None of the techniques or media disclosed in this reference contain the same group of components as the present invention.

Drouet, X., et al. Brit. J. of Haem. 73: 143–147 (1989), disclose a human long-term bone marrow culture medium that is serum-free. However, the medium disclosed therein is not capable of achieving the same degree of long-term culture as in the present invention, growth being maintained for only 3–4 weeks. Furthermore, unlike the media of the present invention, those discussed by Drouet, et al. do not involve stromal cells.

Whitlock, C. A., & Witte, O.N. P.N.A.S. 79: 3608–3612 (1982), relates to long-term culture of B lymphocytes and their precursors from murine bone marrow. This is the famous Witte-Whitlock culture technique. However, again, the media disclosed in this paper are substantially different from those claimed in the present invention, in that they contain serum and can only support B lymphocyte growth.

Teofili, L., et al. Ann. Hematol. 65: 22–25 (1992), describes a serum-free culture system for the growth of human hematopoietic progenitor cells using a preformed extracellular matrix. However, this method does not produce long-term growth, progenitor cells only being maintained in reasonable numbers for 3 weeks. In addition, this method does not use growth factors to support the growth of the bone marrow stromal cells and does not use purified extracellular matrix materials for cell adherence. As a result it does not support the growth of cells from a wide variety of tissues and organs.

In spite of the above prior art, there remains a need to produce chemically defined media for long-term culture of cells. Ideally, such media should be simple to prepare, contain chemically defined ingredients, be economical to produce, and achieve optimal long-term growth and development of cells.

Accordingly, it is an object of the present invention to provide serum-free media for long-term maintenance of proliferation and development of cells, especially of hematopoietic origin.

A further object of the present invention is to provide methods for both short- and long-term culture of cells in a chemically defined medium.

Another object of this invention is to provide a method for stimulating the proliferation and/or development of early progenitor cells for bone marrow transplants and/or gene transfer into these cells for gene therapy procedures.

These and other objects of the invention as will hereinafter be described in greater detail will be apparent to one of ordinary skill in the art.

SUMMARY OF THE INVENTION

In accordance with the objects of the present invention, there is provided a medium for long-term proliferation and development of cells, which comprises cell growth and development-effective amounts of:
 (a) a standard culture medium such as Iscove's modified Dulbecco's medium (IMDM), RPMI, DMEM, Fischer's, alpha medium, Leibovitz's L-15, NCTC, F-10, MEM and McCoy's;
 (b) serum albumin;
 (c) transferrin;
 (d) a source of lipids and fatty acids;
 (e) cholesterol;
 (f) a reducing agent;
 (g) pyruvate;
 (h) nucleosides for synthesis of DNA and RNA;
 (i) one or more growth factors that stimulate the proliferation and development of stromal cells and/or cells from a variety of organs and tissues (preferable mammalian), such as epidermal growth factor, basic fibroblast growth factor, platelet derived growth factor, and insulin; and
 (j) one or more extracellular matrix materials;
wherein said medium is serum-free or serum-depleted.

An optional component of the serum-free medium which is used in cultures where neutrophil development and proliferation is desired (e.g., long-term bone marrow cultures) is:
 (k) a glucocorticoid such as hydrocortisone, cortisol, dexamethasone or other structurally related, natural or synthetic molecule.

Another optional component of the serum-free or serum-depleted medium which may be added separately to the medium when the cells to be supported are hematopoietic cells is:
 (l) stromal cells, which provide a supporting network for hematopoietic cells, as described below in greater detail.

In an exemplary embodiment of the present invention, particularly suited for growth of neutrophils, the cell culture medium comprises the following components in the indicated concentrations:

| Component | Suitable Conc. |
| --- | --- |
| Iscove's Modified Dulbecco's Medium | 0.7–1.17 x |
| Bovine serum albumin | >1 mg/ml |
| Bovine transferrin | >25 µg/ml |
| Soybean lipids | >5 µg/ml |
| Cholesterol | >1 µg/ml |

-continued

| Component | Suitable Conc. |
| --- | --- |
| 2-mercaptoethanol | 100–400 μM |
| Sodium pyruvate | >20 μg/ml |
| Hydrocortisone | 0.05–5 μM |
| Nucleosides | 1–100 μg/ml |
| Epidermal growth factor | >0.5 ng/ml |
| Fibroblast growth factor | >0.1 ng/ml |
| Platelet-derived growth factor | >0.5 ng/ml |
| Insulin | >0.5 μg/ml |
| Collagen IV | >1 μg/cm$^2$ |
| Fibronectin | >0.2 μg/cm$^2$ |

In a preferred embodiment of the present invention, the cell culture medium used to grow cells from different organs or tissues is as already described except that it does not contain any hydrocortisone, or other related glucocorticoid.

In another preferred embodiment, hydrocortisone or another glucocorticoid is not present in the medium and stimulation of the hematopoietic progenitor cells by the growth factor CSF-1, a developmental and proliferative stimulus for macrophages, is also prevented. This can be achieved in a number of ways. A mutant strain of mice can be used in which the CSF-1 gene (B6C3Fe-a/a-op/op mouse strain) or the gene for its receptor or part of the CSF-1 receptor signalling pathway is inactivated, so that no functional protein is produced. A variety of inhibitors of CSF-1 activity could also be employed. For example, neutralizing antibodies against CSF-1 or its receptor could be used to prevent stimulation. In addition it is possible to use antisense oligomers (short sequences of single stranded nucleic acids) to prevent the expression of CSF-1, its receptor or some part of the signal transduction mechanism. The hematopoietic development in these cultures is not restricted to neutrophils and macrophages, but also includes other cell types such as lymphoid, mast cell, megakaryocyte and erythroid cells.

In a particularly preferred embodiment, the cells to be cultured are mammalian in origin.

In a further particularly preferred embodiment, the cells are hematopoietic or lymphopoietic in origin.

BRIEF DESCRIPTION OF THE DRAWINGS

FIG. 8 shows a table which depicts the morphology of the non-adherent hematopoietic cells produced in long-term bone marrow cultures of normal (+/+) or mutant (op/op) mice in the presence or absence of hydrocortisone (HC).

DETAILED DESCRIPTION OF THE INVENTION

Figure 1:
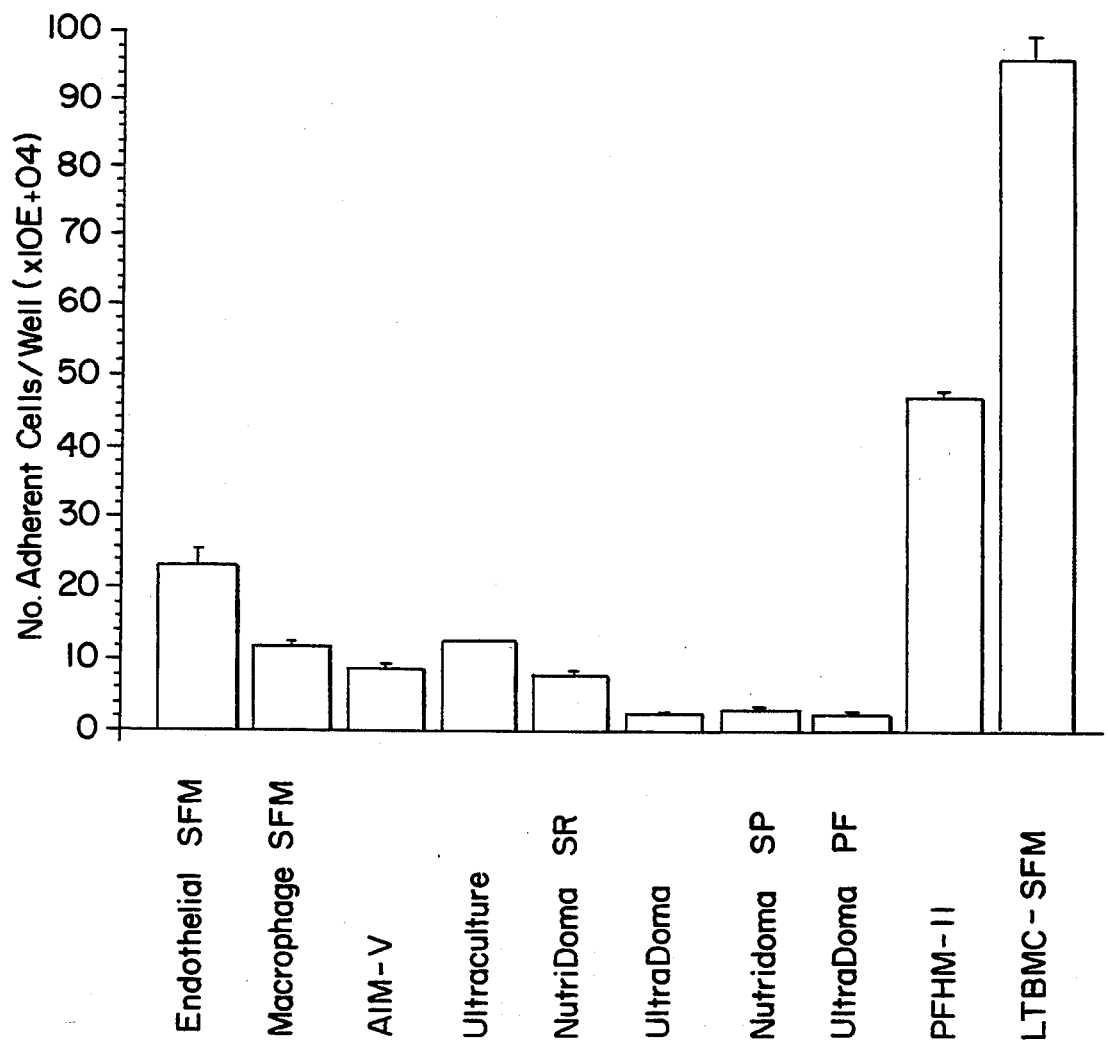
FIG. 1 depicts a comparison of the current invention (LTBMC-SFM) and prior serum-free media, in terms of the number of bone marrow adherent cells (stromal and hematopoietic cells) after 7 days. Note that the present media gave very good hematopoiesis after 2 weeks, whereas hematopoiesis was not observed in any of the prior media tested.

A. Comparison of the Invention with Prior Media

The essential reason why prior serum-free media have failed to give long-term growth of normal hematopoietic cells is that they have not contained the correct combination of ingredients in the proper concentration ranges to support the growth of a wide range of cell types, including hematopoietic cells and stromal cells. This has resulted in many prior serum-free media being limited to supporting-the growth of cell lines, rather than the more difficult to maintain, normal primary cells (i.e., those cells that come directly from an animal). Those media that are capable of maintaining the growth of normal cells only do so for one or a few cell types, and do not provide permissive growth conditions for the long-term culture of hematopoietic cells and stromal cells. In contrast, media of the present invention have the unique ability to support the growth of very different cells from a wide variety of tissues and organs, including primary (normal) cells and cell lines. This ability enables the long-term growth of both the hematopoietic progenitor cells as well as the bone marrow stromal cells (adipocytes, macrophages, endothelial cells and fibroblasts) which are essential for supporting the growth of the hematopoietic cells. This is an ability that prior serum-free media do not possess.

Another shortcoming of prior serum-free media was their species specificity; in contrast, the media of the current invention can support the growth of both mouse and human cells, and they are expected to support the growth and development of cells from other species as well.

While the current invention is a dramatic improvement over prior serum-free media, it is also an improvement over standard serum-supplemented bone marrow cultures. For example, present techniques are limited in the strains of mice from which long-term hematopoiesis can be obtained, whereas no such limitation exists for the current invention, hematopoiesis being obtained from every strain tested. Furthermore, the rate of bone marrow stromal and hematopoietic cell growth under the conditions described in the present invention greatly exceed those in serum-supplemented cultures due to the improvement of numerous aspects of the culture conditions, e.g. adherence, temperature, nutrients and growth factors. In this way, the 4–5 week long period required for classical serum-supplemented long-term bone marrow cultures to produce significant numbers of hematopoietic cells can be reduced to just around 2 weeks.

A further major advantage of the media of this invention over prior methods for the long-term culture of hematopoietic progenitor cells which use serum is the control which it allows in manipulating the proliferation and development of the hematopoietic cells. The reason for this is that all of the ingredients and their concentrations in the culture system are known and can therefore be controlled. This contrasts to serum-supplemented cultures where the contents of the serum are generally unknown, and where the concentrations of the known components are similarly undefined.

For example, by decreasing the concentration of one of the culture ingredients it is possible to efficiently make the culture conditions sub-optimal for growth, thus reducing the number of hematopoietic and/or stromal cells produced.

In a similar way changes in hematopoietic stem cell development can be induced by the removal of the serum-free medium ingredients, hydrocortisone, which is required for optimal growth of neutrophilic cells; as well as the removal of the growth factor CSF-1, a stimulus for macrophage growth, normally produced by the stromal cells in the culture. These alterations in the culture result in not only neutrophil and macrophage development occurring, but also lymphoid, mast cell and possibly erythroid and megakaryocyte development as well. This type of varied development is far more representative of that which occurs in the bone marrow in vivo, and is not observed in any of the prior techniques for the long-term culture of hematopoietic cells.

The use of a defined culture system also makes possible the precise determination of the effect of a known molecule on the cells. Such an analysis is not possible using serum-supplemented cultures where the test molecule may already be present at an unknown concentration.

B. Definitions

In general the "medium" and "media" as used in connection with the present invention are solutions containing growth factors and nutrients, which are used to support the growth and development of cells.

By "long-term" is meant continuous growth and development of the cells being cultured, as well as generation of progenitor cells, for a time period of at least about 8 weeks and up to or surpassing about 12–20 weeks. Preferably, "long-term" means 8–12 weeks.

The "cells" that may be supported (i.e., grown and developed/differentiated) by the media of the present invention are preferably mammalian cells, such as: human, monkey, bovine, ovine, equine, and murine. They are preferably, human or murine cells. Cells from other sources as well as from other mammalian species are also contemplated as would be apparent to one of ordinary skill in the art.

Such cells may be derived from a variety of "tissues," such as lung, liver, kidney, thymus, thyroid, heart, brain, and the like.

Particular examples of normal mammalian cells that may be cultured in the media of the present invention are fibroblasts, endothelial cells, adipocytes, glial cells, neuronal cells, myoblasts, epithelial cells (which may be from a wide range of different tissues), hepatocytes, osteoclasts, and heart muscle cells. The culture media also support a wide range of cell lines including immortalized versions of those already listed; examples of others include bone marrow stromal cell lines, embryonic stem cell lines (such as: D3, E3, SQ1.2S8, MBL-1, 632, and CCEG2), embryonic carcinoma cell lines (such as PGC3), melanoma, mammary, and pituitary cell lines.

Preferred cells of the present invention to be cultured are hematopoietic and lymphopoietic cells which are preferably obtained from the spleen, fetal liver, peripheral blood, umbilical cord or bone marrow.

In general, the present culture media have successfully supported the growth of every cell type so far tested and it is anticipated that it will support the growth of many mammalian cell types.

The term "stromal cells" is used to refer to those cells of the bone marrow which form a supporting network for hematopoietic cells in vivo and in vitro. In this respect they support the hematopoietic cells both physically in providing sites of attachment, as well as biologically in providing the cytokines which these cells require for their growth. In culture they form an adherent layer and include endothelial cells, macrophages, fibroblasts and pre-adipocytes/adipocytes. Accordingly, when the cells to be supported are hematopoietic cells, stromal cells per culture will preferably also be included either as part of the medium, or added to the medium (preferably, $10^4$–$10^7$ stromal cells) during the time the hematopoietic cells are present in the medium.

The term "amino acid" refers to all naturally occurring alpha amino acids in both their D and L stereoisomeric forms, and their analogs and derivatives. An analog is defined as a substitution of an atom in the amino acid with a different atom that usually has similar properties. A derivative is defined as an amino acid that has another molecule or atom attached to it. Derivatives would include, for example, acetylation of an amino group, amination of a carboxyl group, or oxidation of the sulfur residues of two cysteine materials to form cystine.

The amino acids are identified by either the standard single-letter or three-letter designations.

"Serum-free" is used herein to mean that substantially all serum is excluded from the medium (for example 0–0.49%). Further to this is the term "serum-depleted" which means that up to about 5% of serum could be added to the medium (for example 0.5–5%). Preferably less than 3% of the medium will be derived from serum, particularly preferably less than 0.5%. In contrast, serum-containing media of the prior art have typically included >5–40% serum.

By "cell culture effective amount" is meant an amount that is capable of producing long-term cell proliferation and development. Such amounts may be determined for a given constituent by experimentation wherein varying concentrations of a given constituent are added to cell growth media, and the extent and duration of the cell proliferation and development is determined by methods known to a skilled cell culturist.

Preferred ranges and examples of such amounts are provided throughout the specification.

C. Description of Culture Media

An important aspect of the present invention is the discovery that combinations of ingredients in the proper amounts can support both short- and long-term growth (i.e. proliferation) and development of mammalian cells, particularly hematopoietic cells.

In a general sense, there are three primary types of materials included in the present media:

Extracellular matrix materials

These are involved in adhesion of cells, such as to the culture surface. They are typically included in a concentration of 0.2–100 $\mu g/cm^2$.

Examples of extracellular matrix materials from mammalian sources (bovine or human, though preferably murine) that are preferred are: a source of collagen (preferably collagen I and collagen IV), fibronectin, vitronectin and laminin. Especially preferred are:

Mouse collagen IV, which can be used at a concentration of greater than 1 $\mu g/cm^2$, preferably from about 2–100 $\mu g/cm^2$, and more preferably at about 5$\mu g/cm^2$.

Mouse fibronectin, which can be used at a concentration of greater than 0.2 $\mu g/cm^2$, preferably from about 0.5–100 $\mu g/cm^2$, and more preferably at about 2 $\mu g/cm^2$.

However, less pure sources of extracellular matrix can also be used, such as MATRIGEL, which is a complex mixture of matrix and associated materials. Matrix secreted by a previously adherent cell can also be used. The cell is grown on the plastic culture surface and secretes extracellular matrix, removal of these cells then provides a layer of extracellular matrix to which a second cell type can adhere.

Growth factors

These are molecules involved in stimulating proliferation of the stromal cells or other cells from a variety of tissues that are desired to be supported by the media. In the case of bone marrow stromal cells they produce growth factors for the hematopoietic cells in the culture, e.g. GM-CSF, G-CSF, SCF, IL-1, CSF-1, IL-6, and a variety of others. In cases where a purified population of hematopoietic cells is cultured using the serum-free medium these growth factors have to be added (typically in concentrations of 0.5 ng/ml–100 $\mu g/ml$, depending on the growth factor and the cells involved), since the stromal cells will have been removed.

The choice of growth factors required to support the growth and development of particular types of cells will vary depending on the cell type, and will be readily determinable by those skilled in the art of cell biology and culture. Growth factors for the stromal and tissue cells that are particularly useful in accordance with the present invention, and to which additional specific growth factors can always be added as desired or necessary for growth include:

Recombinant human epidermal growth factor (EGF), which can be used at a concentration of greater than 0.5 ng/ml, preferably from about 5–200 ng/ml, and more preferably at about 15 ng/ml.

Recombinant human basic fibroblast growth factor (bFGF), which can be used at a concentration of greater than 0.1 ng/ml, preferably from about 0.5–40 ng/ml, and more preferably at about 2 ng/ml.

Recombinant human platelet derived growth factor (PDGF) (preferably the B—B isoform), which can be used at a concentration of greater than 0.5 ng/ml, preferably from about 2–200 ng/ml, and more preferably at about 10 ng/ml.

Insulin (human or preferably from bovine pancreas) can be used at a concentration of greater than 0.5 $\mu g/ml$, preferably from about 2–100 $\mu g/ml$, and more preferably at about 10 $\mu g/ml$.

Less pure sources of growth factors such as conditioned media from cell lines producing these growth factors can also be used, but do not give such a defined culture. In addition it is possible to use growth factors from other species, e.g. bovine and mouse.

Nutrients

These are molecules involved in normal metabolic functions of the cultured cells.

Nutrients and metabolic additives useful in the media of the present invention include a standard culture medium (described below); serum albumin (preferably bovine or human); transferrin (preferably bovine or human); a source of lipids and fatty acids useful in cell growth and development (preferably soybean lipids); cholesterol; a reducing agent (preferably 2-mercaptoethanol or monothioglycerol); pyruvate (preferably sodium pyruvate); a glucocorticoid (preferably, a cortisone derivative such as hydrocortisone 21-hemisuccinate, particularly preferably the sodium salt); and nucleosides.

The following is a more detailed description of some of the individual components of the nutrients in the media of the present invention:

The "standard culture media" which may be employed in accordance with the present invention are standard culture media for growing cells that typically provide at least one component from the following categories:

(a) an energy source, usually in the form of a carbohydrate such as glucose;

(b) substantially all essential and non-essential amino acids, usually the basic set of twenty amino acids, plus cystine instead of cysteine;

(c) vitamins and/or other cell-growth supporting organic compounds required at low concentrations;

(d) a buffering agent such as HEPES, Tris, or MOPS (preferably HEPES), which act to stabilize the hydrogen ion concentration and therefore the pH of the solution by neutralizing, within limits, both acids and bases;

(e) inorganic salts and trace elements, where trace elements are defined as inorganic compounds or naturally occurring elements that are typically required at very low concentrations, usually in the micromolar range (e.g., 1–1000 $\mu M$).

Particular examples of the standard culture media which are useful in accordance with the present invention are: RPMI, DMEM, MEM, Leibovitz's L-15, Fischer's, F-10, alpha medium, NCTC and McCoy's, but preferably Iscove's modified Dulbecco's medium (IMDM); Iscove, N. N. & Melchers, F. J. Exp. Med. 147, 923 (1978).

In accordance with this invention, the standard culture medium is supplemented with particular components from the following categories:

The "serum albumin" of the present invention may be obtained from any mammalian source, such as human, monkey, bovine, ovine, equine, murine. Preferably the source of serum albumin is human or bovine. The serum albumin can be used at a concentration of greater than 1 mg/ml, preferably from about 3–50 mg/ml, and more preferably at about 10 mg/ml. It is notable that although the present media are generally serum-free, certain serum components which are chemically well defined and highly purified (>95% pure), such as serum albumin, may be included.

Transferrin is another protein component of the media set forth herein which is also preferably of mammalian origin, particularly preferably human or bovine. This component can be incorporated at greater than 25 μg/ml, preferably from about 25–1000 μg/ml, and more preferably at about 100–300 μg/ml.

"A source of lipids and fatty acids" means any of a variety of such sources. For example, crude extracts of lipids may be used to supplement the media of this invention. The lipid extract may be obtained from any biological source, although one preferred source is plant material, and particularly soybeans (soybean lipid extract may be purchased from Boehringer-Mannheim). Typically, the extract will contain from about twenty percent to about ninety-five percent lipid, the majority of which will be phospholipid, the remainder being fatty acids, with traces of sterol. The extract may be added to the cell culture medium at a concentration of greater than about 5 μg per ml, preferably from about 5 μg per ml to about 100 μg per ml, and more preferably 5 μg per ml to about 50 μg per ml.

The addition of a molecule capable of regulating the cell plasma-membrane fluidity is an important component. Preferably, this invention employs the lipid cholesterol at a concentration of greater than about 1 μg/ml, or preferably from 3–30 μg/ml, or more preferably at about 7.8 μg/ml.

The term "a reducing agent" means any reducing agent that is compatible with a cell culture medium. Preferred examples are: 2-mercaptoethanol or monothioglycerol. Generally, the reducing agent is present in a concentration of about 10 to 400 μM, preferably 30 to 300 μM, and particularly preferably, about 100 μM.

"Pyruvate" refers to any cell-culture compatible salt of pyruvic acid, preferable sodium or potassium pyruvate. Pyrucic acid itself may also be added, forming a salt to some degree in situ. Pyruvate is required for general metabolic processes as a potential source of energy and for synthesizing more complex molecules. Generally, the pyruvate is present in a concentration of >20 μg/ml, preferably 30 to 500 μg/ml, and particularly preferably, about 110 μg/ml.

The term "nucleosides" refers to naturally occurring nucleosides that form the basis for synthesis of DNA and RNA. Such nucleosides include the following: adenosine, guanosine, cytidine, uridine, 2'-deoxyadenosine, 2'-deoxyguanosine, 2'-deoxycytidine and thymidine. Phosphorylated (mono, di, or tri) analogues could also be used. The nucleosides may be added to the cell culture medium at a concentration of about 1 to 100 μg/ml, preferably from about 5 to 30 μg/ml and particularly preferably about 10 μg/ml.

The growth factors epidermal growth factor, fibroblast growth factor, platelet-derived growth factor and/or insulin which have already been discussed in detail in section B are preferably all included in the standard medium.

A component which is not required in all embodiments of the invention is a natural or synthetic corticoid such as the cortisone derivatives: prednisone, dexamethasone or preferably hydrocortisone. These molecules are involved in carbohydrate, protein and fat metabolism, are anti-inflammatory and immunosuppressive, and are thought to regulate the levels of certain cytokines and/or their receptors, such as TNF-alpha, GM-CSF and G-CSF. A corticoid such as hydrocortisone can be used at a concentration of about 0.05–5 μM, or preferably 0.3–1 μM, or particularly preferably at about 0.5 μM.

The following table provides a summary list of some particularly preferred components along with suitable concentrations, preferred concentrations and the most preferred concentrations for each component. These quantities are applicable to equivalent components of each type defined herein listed in the table.

| Table of Culture Components and Concentrations | | | |
|---|---|---|---|
| Component | Suitable Conc. | Preferred Conc. | Exemplary Conc. |
| Standard Culture Medium (e.g., Iscove's Modified Dulbecco's Medium) | 0.7–1.17 x | 0.8–1.09 x | 1 x |
| Serum albumin (e.g., bovine) | >1 mg/ml | 3–50 mg/ml | 10 mg/ml |
| Transferrin (e.g., bovine) | >25 μg/ml | 25–1000 μg/ml | 100 μg/ml |
| Source of lipids (e.g., soybean lipids) | >5 μg/ml | 5–100 μg/ml | 25 μg/ml |
| Cholesterol | >1 μg/ml | 3–30 μg/ml | 7.8 μg/ml |
| Reducing Agent (e.g., 2-mercaptoethanol) | 10–400 μM. | 30–300 μM. | 100 μM |
| Pyruvate (e.g., sodium pyruvate) | >20 μg/ml | 30–500 μg/ml | 110 μg/ml |
| Glucocorticoid (e.g., Hydrocortisone) | 0.05–5 μM. | 0.3–1 μM. | 0.5 μM |
| Nucleosides (e.g., DNA/RNA derived) | 1–100 μg/ml | 5–30 μg/ml | 10 μg/ml |
| Growth Factors (e.g., Epidermal growth factor | >0.5 ng/ml | 5–200 ng/ml | 15 ng/ml |
| Fibroblast growth factor | >0.1 ng/ml | 0.5–40 ng/ml | 2 ng/ml |
| Platelet-derived growth factor | >0.5 ng/ml | 2–200 ng/ml | 10 ng/ml |
| Insulin | >0.5 μg/ml | 2–100 μg/ml | 10 μg/ml |
| Extracellular Matrix Materials (e.g., Collagen IV Fibronectin) | >1 μg/cm² | 2–100 μg/cm² | 5 μg/cm² |
| | >0.2 μg/cm² | 0.5–100 μg/cm² | 2 μg/cm² |

On specific, exemplary cell culture medium within the scope of the present invention is set forth as follows

| Component | Concentration (mg/L) (unless stated otherwise) |
|---|---|
| ISCOVE'S MODIFIED DULBECCO'S MEDIUM | |
| INORGANIC SALTS: | |
| CaCl₂ (anhydr.) | 165.00 |
| KCl | 330.00 |
| KNO₃ | 0.076 |

| Component | Concentration (mg/L) (unless stated otherwise) |
|---|---|
| MgSO$_4$ (anhydr.) | 97.67 |
| NaCl | 4505.00 |
| NaHCO$_3$ | 3024.00 |
| NaH$_2$PO$_4$ . H$_2$O | 125.00 |
| Na$_2$SeO$_3$ . 5 H$_2$O | 0.0173 |
| OTHER COMPONENTS: | |
| D-Glucose | 4500.00 |
| Phenol red | 15.00 |
| HEPES | 5958.00 |
| Sodium pyruvate | 110.00 |
| AMINO ACIDS: | |
| L-Alanine | 25.00 |
| L-Asparagine . H$_2$O | 28.40 |
| L-Arginine . HCl | 84.00 |
| L-Aspartic acid | 30.00 |
| L-Cystine . 2HCl | 91.24 |
| L-Glutamic acid | 75.00 |
| L-Glutamine | 584.00 |
| Glycine | 30.00 |
| L-Histidine HCl . H$_2$O | 42.00 |
| L-Isoleucine | 105.00 |
| L-Leucine | 105.00 |
| L-Lysine HCl | 146.00 |
| L-Methionine | 30.00 |
| L-Phenylalanine | 66.00 |
| L-Proline | 40.00 |
| L-Serine | 42.00 |
| L-Threonine | 95.00 |
| L-Tryptophane | 16.00 |
| L-Tyrosine (Disodium salt) | 104.2 |
| L-Valine | 94.00 |
| VITAMINS: | |
| Biotin | 0.013 |
| Ca D-Pantothenate | 4.00 |
| Choline chloride | 4.00 |
| Folic acid | 4.00 |
| i-inositol | 7.20 |
| Nicotinamide | 4.00 |
| Pyridoxal HCl | 4.00 |
| Riboflavin | 0.40 |
| Thiamine HCl | 4.00 |
| Vitamin B$_{12}$ | 0.013 |
| ADDITIONAL COMPONENTS | |
| Bovine Serum Albumin | 10000.00 |
| Bovine Transferrin | 100.00 |
| Soybean Lipids | 25.00 |
| Cholesterol | 7.80 |
| Hydrocortisone | 0.24 |
| 2-mercaptoethanol | 7.84 |
| Sodium pyruvate | 110.00 |
| Adenosine | 10.00 |
| Cytidine | 10.00 |
| Guanosine | 10.00 |
| Uridine | 10.00 |
| 2'-deoxyadenosine | 10.00 |
| 2'-deoxyguanosine | 10.00 |
| 2'-deoxycytidine | 10.00 |
| Thymidine | 10.00 |
| Epidermal growth factor | 15 × 10$^{-3}$ |
| Fibroblast growth factor | 2 × 10$^{-3}$ |
| Platelet-derived growth factor | 10 × 10$^{-3}$ |
| Insulin | 10.00 |
| Collagen IV | 5 μg/cm$^2$ |
| Fibronectin | 2 μg/cm$^2$ |

D. Preparation of the Media and Culture Technique

The following is an exemplary method for preparing the media and carrying out the culture technique of the present invention. Equivalent components as set forth herein could be substituted within the concentration ranges set forth herein for those described below.

Extracellular matrix (ECM)

The evening before initiating the cultures, six well plates (Corning, 10 cm$^2$ surface area/well) are coated with 0.73 ml solution of Iscove's Modified Dulbecco's Medium (IMDM) containing glutamine (292 μg/ml), penicillin G (100 units/ml) and streptomycin sulfate (100 μg/ml), all three are supplied together (Irvine Scientific) at a 100×concentration. Dissolved extracellular matrix materials can then be added to this solution. A number of ECM molecules have been tested. It has been determined that a source of collagen is important, mouse collagen IV (5 μg/cm$^2$ Sigma, Cat.#C0543) being preferred. Additional ECM molecules can then be added, e.g. fibronectin and laminin, mouse fibronectin (2 μg/cm$^2$ Sigma, Cat.#F1141) in combination with collagen IV is used normally, in a final volume of 0.8 ml.

The next morning the wells are washed once with IMDM and the serum-free medium and cells added.

Nutrient/Metabolic Additives

A number of nutrients are added to the medium, they are prepared at a 100×final concentration, the final concentrations in the culture are shown below:

Bovine serum albumin (10 mg/ml, Sigma, cat.#A8412).

Bovine (100 μg/ml, Sigma cat.#T-1283) or human transferrin (300 μg/ml, Boehringer-Mannheim cat.#652 202) (for mouse and human cultures, respectively).

Soybean lipids (25 μg/ml, Boehringer-Mannheim cat.#652 229).

Cholesterol (7.8 μg/ml, Sigma cat.#C-3045).

2-mercaptoethanol (10$^{-4}$ M. Sigma cat.#M-7522).

Sodium pyruvate (110 μg/ml (1 mM) Sigma cat.#P3662).

Hydrocortisone 21-hemisuccinate, sodium salt (5×10$^{-7}$ M, Sigma cat.#H-4881).

Nucleosides (10 μmg/ml each, Sigma cat.#s: adenosine A-4036, guanosine G-6264, cytidine C-4654, uridine U-3003, 2'-deoxyadenosine D-0651, 2'-deoxyguanosine D-0901, 2'-deoxycytidine D-0776, thymidine T-1895).

Growth Factors (for stromal cells)

Growth factor stock solutions are prepared at a 100×concentration in IMDM and 1% BSA, and then diluted in the culture medium to the required concentration shown below.

Epidermal Growth Factor (EGF) (15 ng/ml, Sigma, cat.#E4127 (mouse, from submaxillary gland), cat.#E1264 (human, recombinant)).

Recombinant Human Fibroblast Growth Factor (FGF) (2 ng/ml, Amgen Inc., or Genzyme cat.#1208-00).

Recombinant Human Platelet Derived Growth Factor (PDGF) (B-B isoform) (10 ng/ml, Amgen Inc.).

Insulin (from bovine pancreas, 10 μg/ml, Sigma, cat.#I4011).

Preparing Serum-Free Medium

The stock solutions of the nutrients, growth factors etc. are prepared fresh and then pooled at the required relative concentration (50 μl/well for all additives and 667 μl/well for the BSA) and frozen in small aliquots until required (to avoid freezing and thawing).

It is important to note that substantially all of the above-described components of the serum-free medium are important for optimal growth of stromal and hematopoietic cells in the cultures. However, not all of the components are absolutely essential. The most important components are extracellular matrix materials, IMDM (or a similar standard culture medium), and serum albumin. Removal of any other component will result in reduction of growth varying from mild to severe.

Culture Technique

The long-term bone marrow cultures are obtained by first flushing the marrow from the femurs of 8–12 week old B6D2F$_1$ mice, obtained from Charles River Laboratories, (other strains can be used) into IMDM. If lymphoid long-term bone marrow cultures are required then 2–4 week old B6C3Fe-a/a-op/op mice are used, obtained from Jackson Labs or bred at Amgen. The cells are prepared in this case by cutting the femurs and tibias into small pieces and then grinding them using a pestle and mortar. The cells from any strain of mice used are then washed three times by centrifuging the cells for 5 min at 1500 rpm., they are then resuspended in a 10 ml volume. This procedure is repeated twice and the cells are finally resuspended at a concentration of $5 \times 10^6$/ml in IMDM supplemented with glutamine, penicillin and streptomycin.

Cells from other tissues and organs are prepared by cutting the organs such as fetal liver and spleen into small pieces and then homogenizing them using a tissue homogenizer. The cells are again washed three times and resuspended at a concentration of $10^6 – 5 \times 10^6$/ml for fetal liver and $10^7 – 5 \times 10^7$ for spleen. Other organs and tissues such as liver, lung, kidney, brain and heart are prepared in exactly the same way, except that they are treated with 2 mg/ml collagenase (Sigma) (dissolved in IMDM and 20 mg/ml bovine serum albumin), at 37° C. for 1.5 hr. to digest the tissue prior to homogenizing. The cells are used at a concentration of $5 \times 10^6 – 10^7$/ml.

One ml of the cell suspension obtained is then added to each of the previously prepared wells together with 1.22 ml of the frozen serum-free medium. The volume is made up to 5 ml/well with 2.78 ml of fresh IMDM, supplemented, as before, with glutamine, penicillin and streptomycin. This results in a final cell density/well (5 ml volume) which is the same as already stated for each cell stock suspension, i.e. 1 ml. at $5 \times 10^6$/ml into a well will give a final density of $5 \times 10^6$/well.

The cultures are then incubated, preferably in the dark, at 33° C. for long-term bone marrow cultures, or at 37° C. for bone marrow cultures of up to 3 weeks duration, and when culturing tissues or organs (generally 30°–45° C.; preferably 33°–40° C.; particularly preferably 33°±1° C. or 37°±1° C.) using a 5% CO$_2$ (generally 1–20%; preferably 3–10%, particularly preferable 4–6%) balanced air incubator. The cells are allowed to adhere and E. Use Of the Media The following are possible uses of this invention.

The media of this invention are particularly useful for culturing cells at high densities (at least 100,000 cells per milliliter of medium, and often 600,000 or 10,000,000 cells per milliliter of medium). In addition, culturing cells in these media typically results in an enhanced yield of product as compared with culturing the cells in publicly available media.

The completed medium may be used for culturing a variety of mammalian cells. The medium is inoculated with the selected cells. Preferably, the inoculum volume will be on the order of about one-fifth of the volume of the medium, although some variation from this inoculum volume is acceptable. After inoculation, the culture is maintained in an appropriate environment with respect to temperature.

The media of this invention may be used for culturing the cells as a monolayer, in semi-solid media or in suspension. The cells may be grown as a small-scale culture, i.e. in volumes of about 2 liters or less. Alternatively, and preferably, the cells are cultured in large volumes such as up to about 16 liters in spinner flasks or about 80 liters or more in fermenters designed for commercial production of biological compounds from animal cells. The cells are preferably grown as either small-scale suspension cultures or large-scale suspension cultures at a density of at least 100,000 cells per milliliter, which is considered to be a high density culture. There is also the possibility that the cells could be maintained in bioreactors where there is continuous removal of toxic materials produced by the cells, as well as a constant supply of nutrients.

The cells themselves or a biological compound inside of the cells may be the desired end-product of the culturing. If so, they may be harvested and separated from the culture medium. Alternatively, a protein or other organic compound secreted by the cells into the medium may be the desired end-product of the culturing. In this situation, the medium may be separated from the cells, and the compound of interest can then be purified from the medium.

This invention also has potential utility in bone marrow transplantation procedures. This possibility is suggested by the ability of these media and techniques to support both the survival, expansion and/or development of the hematopoietic stem cells and other progenitors in the presence of stromal cells or added exogenous growth factors. The hematopoietic cells produced by this invention could be used as a graft to treat those patients who are leukopenic following chemotherapy or radiation therapy for cancer. They could also be used as a graft in congenital or metabolic immunological or hematological disorders.

Another possible use of this invention is in the transfer of genes into stem cells for somatic cell gene therapy, particularly into hematopoietic stem cells for the treatment of immunological or hematological disorders, e.g. severe combined immunodeficiency (SCID), adenosine deaminase (ADA) deficiency, and AIDS.

A further potential use of this invention is in the determination of the function of genes whose biological role is unknown. The cell cultures established using this invention could be treated with antisense oligomers. These are short stretches of DNA, normally about 15–30 bases in length, which inhibit normal transcription and therefore expression of genes for which the antisense is a mirror image. The antisense DNA could either be added directly to the culture or alternatively in the form of a retroviral vector. Such an approach could potentially reveal the function of the novel gene.

The following examples illustrate a preferred mode for practicing the invention, but should not be construed to limit the invention. All literature citations herein are expressly incorporated by reference.

EXAMPLES

Example 1

Establishment of llong-term bone marrow cultures using commercial serum-free medium or the current invention.

Serum-free long-term bone marrow cultures were set up as already described (using $5\times10^{-7}$M hydrocortisone and a temperature of 37° C). The initial growth and proliferation, together with the hematopoiesis produced by the current invention-were compared to that obtained using a variety of commercially available serum-free media, in the presence of the same extracellular matrix (5 $\mu$g/cm$^2$ collagen IV and 2 $\mu$g/cm$^2$ fibronectin) as used in the present invention. The commercial serum-free media used included endothelial SFM (Gibco, cat.#320-7601PJ), macrophage SFM (Gibco, cat.#320-2065PG), AIM-V (Gibco, cat.#320-2055AG), UltraCULTURE (Whittaker, cat.#12-725B), NutriDOMA SR (Boehringer-Mannheim, cat.#1271091), UltraDOMA (Whittaker, cat.#12-723B), Nutridoma SP (Boehringer-Mannheim cat.#100-104), UltraDOMA PF (Whittaker, cat.#12-727B), and PFHM-II (Gibco, cat.#320-2040AG).

The efficiency of establishing the cultures was determined by counting the number of adherent cells in the cultures after 7 days using a hemocytometer. In the absence of a suitable growth environment the small number of cells which adhere and proliferate to form the eventual culture, approximately $3\times10^4$/well, are either maintained in a static, non-proliferative state or rapidly die.

FIG. 1 shows that the number of adherent bone marrow stromal and hematopoietic cells after one week of culture was far greater in the medium of the current invention, than in any of the commercial serum-free media tested. The number of adherent cells present ranged from 2 to 22% of the number obtained when using the media of the current invention. The only exception to this was the PFHM-II medium which gave approximately 48% of the number of adherent cells obtained using the invention discussed here.

When the morphology of the cells in the different types of serum-free medium were examined it was observed that while the cultures stimulated with the media of the current invention gave a variety of stromal cell types including fibroblasts, endothelial cells, adipocytes and macrophages, the commercial serum-free media supported a more limited cell growth. All prior media were able to support macrophage survival as well as the growth of a small number of fibroblasts, however there were few if any endothelial cells, except when using the endothelial cell SFM. and no adipocytes. All of the prior serum-free media stimulated a limited proliferation of the stromal cells compared to the current invention.

In addition to the efficiency of establishing an adherent stromal cell layer the extent of hematopoiesis occurring in these cultures after 3 weeks was also evaluated by counting the number of mature hematopoietic cells released into the medium. It was determined that only the medium of the current invention showed any signs of hematopoiesis taking place, as observed visually and in relation to a non-adherent cell count of $15.5\pm2.1\times10^6$/well for the current invention and none for the other serum-free media types.

Example 2

All the groups of serum-free medium components are required for efficient establishment of long-term bone marrow cultures.

To determine whether or not all the groups of serum-free medium components (IMDM, growth factors, extracellular matrix and medium supplements) were required for the efficient establishment of long-term bone marrow cultures they were initiated in the presence of all of the above, or with one of the groups of components absent. IMDM was replaced with phosphate buffered saline (PBS), while the other groups were replaced by IMDM. Growth factors included epidermal growth factor, fibroblast growth factor, platelet-derived growth factor and insulin. The extracellular matrix materials used were collagen IV and fibronectin. While the medium supplements included bovine serum albumin, transferrin, soy bean lipids, cholesterol, 2-mercaptoethanol, nucleosides and hydrocortisone. Cultures were set up at 37° C. in the presence of $5\times10^{-7}$M. hydrocortisone.

Figure 2:
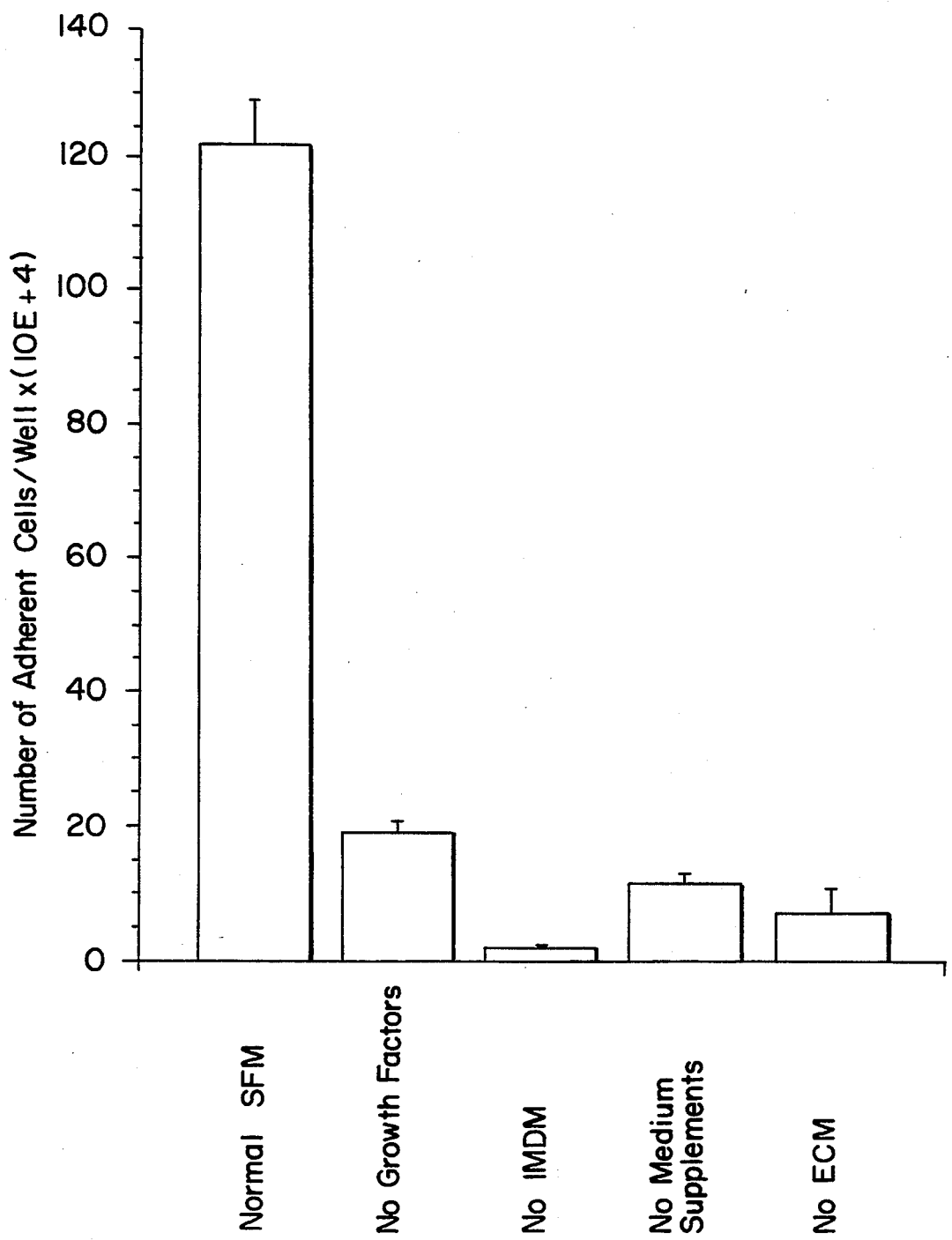
FIG. 2 depicts the effect of removing one of the groups of serum-free medium components on the establishment of long-term bone marrow cultures as indicated by the adherent cell counts after 7 days. Error bars show standard deviations.

FIG. 2 clearly shows that the number of adherent bone marrow stromal and hematopoietic cells after 7 days is far greater in the presence of all the serum-free medium component groups than when one is absent. In the absence of one of the components only 2-16% of the number of adherent cells in the complete medium were obtained.

In order to determine which groups of serum-free medium components were the most important in improving on the prior serum supplemented "Dexter type" long-term bone marrow cultures, different facets of the serum-free culture system were added to Dexter cultures. These components included, extracellular matrix, the media type (the Dexter method uses Fischer's medium, whereas the current invention uses IMDM), growth factors, nutrients (including bovine serum albumin, transferrin, cholesterol, 2-mercaptoethanol, nucleosides, and soybean lipids) and temperature (the Dexter method uses 33° C. and the current invention uses 7° C.). The effectiveness of the addition of one or more of these serum-free medium components was determined by counting the number of adherent cells after 7 days.

The Dexter cultures were established by preparing a bone marrow cell suspension from the femurs of 8-12 week old B6D2F$_1$ mice as described earlier. The cells together with serum at a final concentration of 20% (v/v), $10^{-6}$M. hydrocortisone and Fischer's medium were added to Corning 6 well plates to give a final volume of 5 ml and a cell density of $5\times10^6$/ml. These cultures were incubated at 33° C. in a humidified incubator containing 5% $CO_2$ in air. Different components of the serum-free culture system were then added to or used to replace components of the Dexter culture, as in the case of IMDM replacing Fischer's medium, and 37° C. being used instead of 33° C. In all cases the hydrocortisone concentration used was $10^{-6}$M except for the normal serum-free cultures where it was $5\times10^{-7}$M. Serum-free long-term bone marrow cultures were established as already described.

Figure 3:
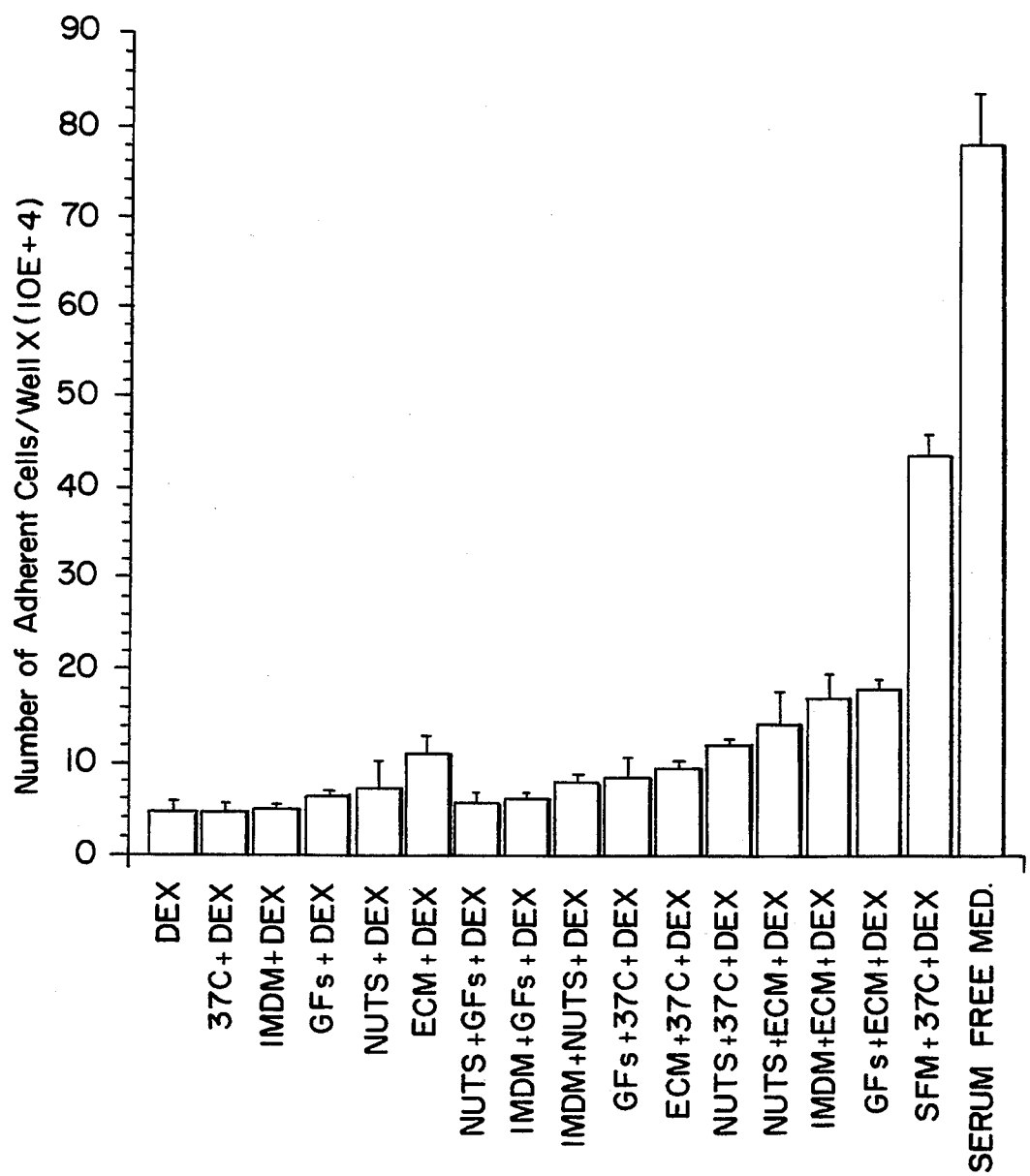
FIG. 3 depicts the effect of adding serum-free medium components to serum supplemented "Dexter" cultures (DEX), including growth factors (+GFs), Iscove's medium (+IMDM) instead of Fischer's medium, extracellular matrix materials (ECM), additional nutrients (NUTS), and a temperature of 37° C. rather than 33° C. The cultures SFM+37° C.+DEX were set up under standard serum-free medium conditions, but with horse serum. Error bars show standard deviations.

FIG. 3 shows that the amount of stromal cell proliferation is far greater in the serum-free culture conditions than in the serum supplemented Dexter cultures. However this large increase in cell number cannot be accounted for by one, or any pair of serum-free medium components. Instead all of the components together are required to provide the conditions which give the largest number of cells. In addition it was found that the addition of serum to normal serum-free cultures resulted in a decrease in the number of cells probably because the serum contains undefined inhibitory materials.

Example 3

The importance of Extracellular Matrix Materials in Serum-Free Long Term Bone Marrow Cultures.

To determine the importance of extracellular matrix (ECM) materials in the establishment of serum-free long-term bone marrow cultures the number of adherent cells in cultures containing different types and amounts of ECM were determined after 7 days.

Figure 4:
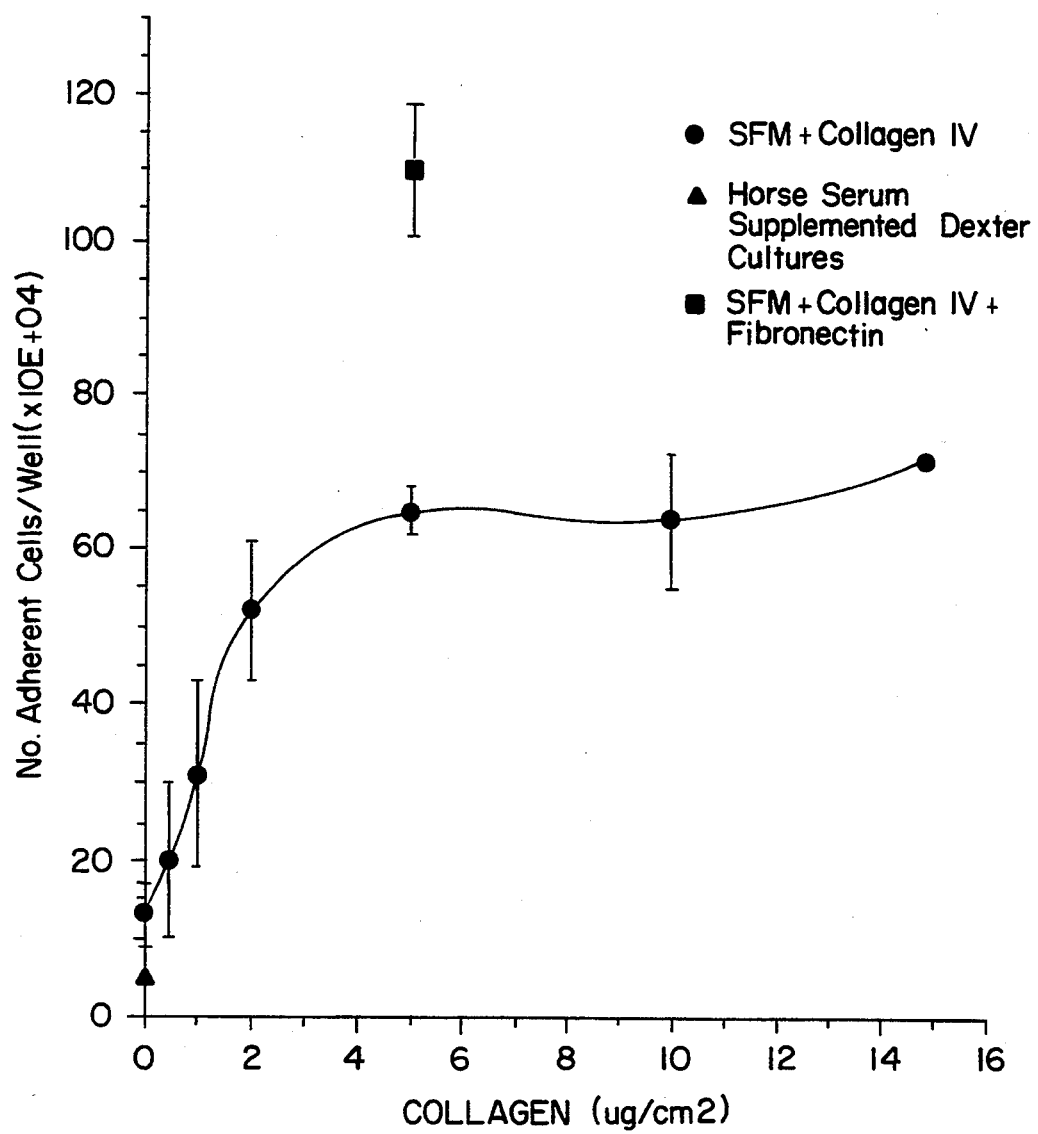
FIG. 4 depicts the relative number of adherent cells (a combination of bone marrow stromal and hematopoietic cells) in serum supplemented and serum-free media after 7 days of culture. The importance of extracellular matrix materials such as collagen and fibronectin in serum-free cultures is also shown. Fibronectin is at a conc. of 2 μg/cm$^2$. Error bars show standard deviations.

The evening prior to setting up the cultures the culture wells (Corning 6 well plates) were coated with different types and concentrations of ECM as indicated in FIG. 4 in a final volume of 0.8 ml. Mouse collagen IV (Sigma) was used at a range of concentrations from 0–15 $\mu g/cm^2$, whereas mouse fibronectin (Sigma) was used at 2 $\mu g/cm^2$. Serum-supplemented cultures did not receive any ECM coating. The following morning the ECM solution was removed and the serum (20% horse serum, Gibco, $10^{-6}M$ hydrocortisone and Fischer's medium, Gibco) and serum-free cultures ($5\times10^{-7}M$ hydrocortisone) were set up as already described.

FIG. 4 shows that in the absence of ECM the number of adherent cells after 7 days in serum-free cultures is only about twice that of horse serum supplemented "Dexter" cultures, and is much less than occurs in the presence of ECM. On the addition of collagen IV there is an increase of up to 4 fold in the number of adherent cells. When fibronectin as well as collagen IV is added to the wells the number of adherent cell increases even further to 6 times the number in the absence of ECM.

Example 4

The production of hematopoietic cells in serum-free long-serum bone marrow cultures In order to assess the ability of the serum-free medium to maintain long-term hematopoiesis bone marrow cultures were set up as previously described at a temperature of 37° C. and in the presence of $5\times10^{-7}M$ hydrocortisone. The cultures were fed twice a week and the extent of hematopoiesis in the cultures determined weekly by (a). counting the total number of non-adherent cells, and (b). counting the number of non-adherent colony forming cells, 4 days after the previous feed.

The number of non-adherent cells in the cultures was counted using a hemocytometer. The number of colony forming cells was determined using a standard semi-solid medium assay well known to those experienced in the art. Briefly, the cells were suspended at a concentration of $5\times10^4$ cells/ml in a semi-solid media containing 20% (v/v) fetal calf serum (Gibco), 10% (v/v) deionized bovine serum albumin (Sigma), 0.8% methylcellulose, the growth factor mouse IL-3 (0.75 ng/ml, Piprotech), and IMDM. 1 ml of this mixture was dispensed into a 35 mm diameter petri dish (Falcon) and incubated in a sealed, humidified box, containing 10% $CO_2$, 7% $O_2$, 83% $N_2$, at 37° C. for 14 days.

Figure 5:
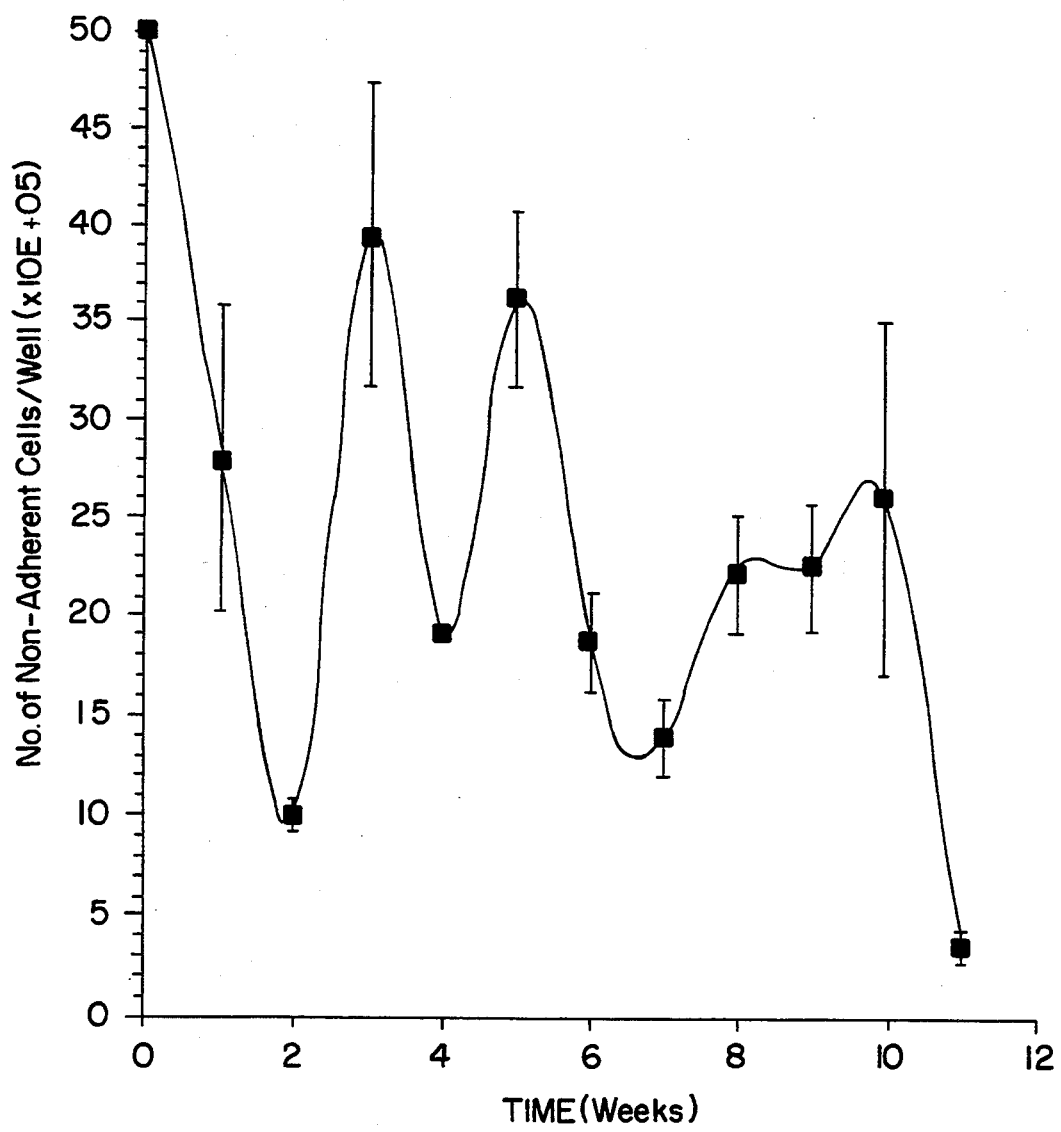
FIG. 5 depicts the long-term hematopoiesis which occurs using the current invention, as indicated by the total number of non-adherent hematopoietic cells (mainly mature cells) produced over an 11 week period, ±standard deviation.

FIG. 5 shows the number of non-adherent cells produced in the serum-free cultures over an 11 week period. During this period the non-adherent cell production was maintained at an average value of about 50% of the input population ($25\times10^5$ cells). The peak of cell production occurred 3 weeks after initiation of the cultures, and a frequent increase and decrease in cellularity occurred throughout the culture period. In other experiments hematopoiesis has been maintained for greater than 14 weeks.

Figure 6:
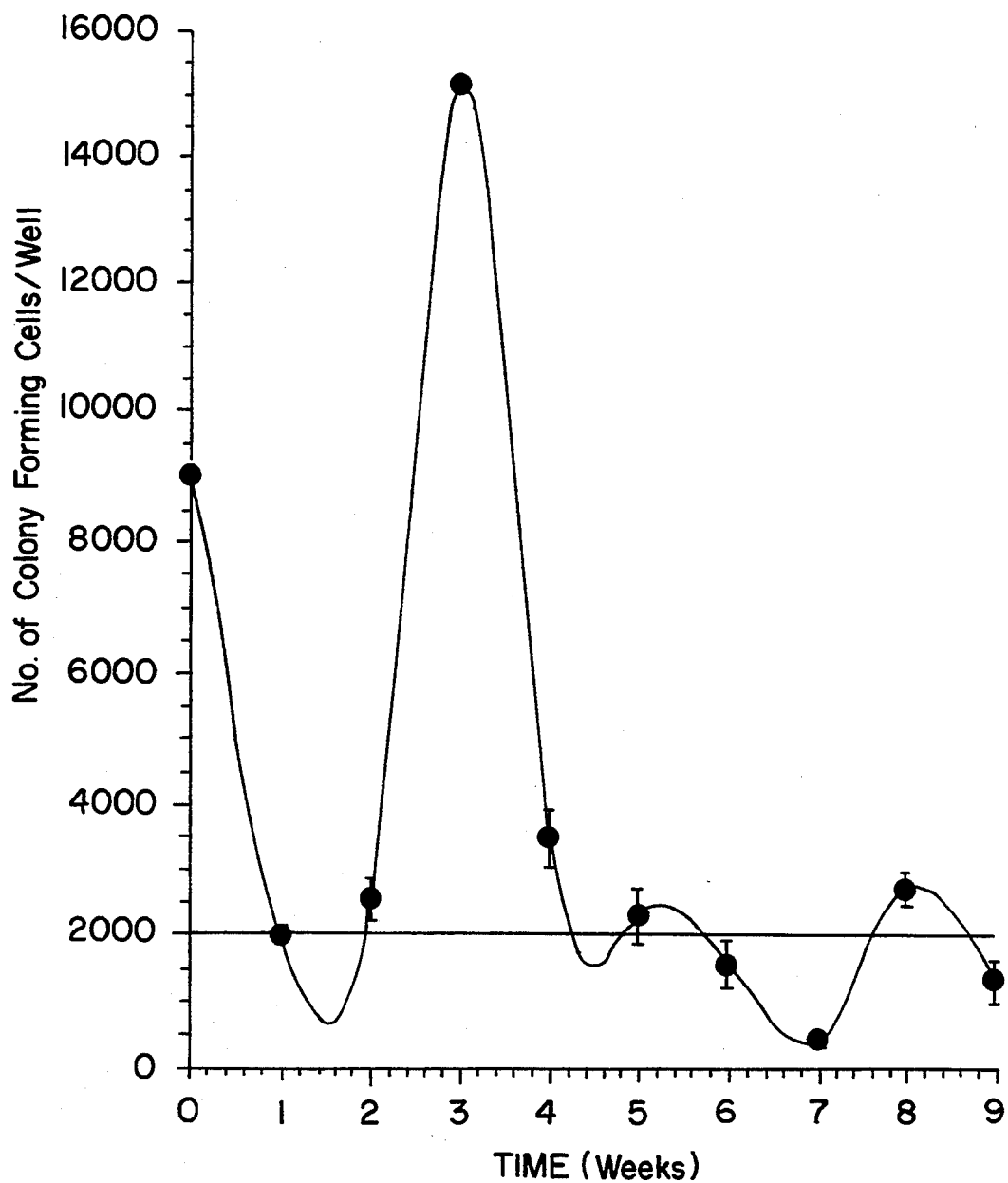
FIG. 6 depicts the long-term hematopoiesis which occurs using the current invention, as indicated by the number of non-adherent hematopoietic progenitor cells (colony forming cells) produced over a 10 week period, ±standard deviation.

FIG. 6 shows the number of non-adherent colony forming cells produced in the same cultures (see FIG. 5) over a 9 week period. The peak of production occurred 3 weeks after initiation of the cultures and was approximately 170% of the number of colony forming cells initially put into the culture. After 3 weeks the number of colony forming cells rapidly dropped off and reached an average of 2000/well after about 5 weeks.

An important point to note is that this assay gives an indication of the amount of hematopoiesis occurring in these cultures and does not reflect the absolute number of colony forming cells since many of them will be adhering to the stromal cells and will therefore not be detected in this assay which only uses non-adherent cells.

Example 5

The production of hematopoietic cells in serum-free long-term bone marrow cultures using different mouse strains.

This invention was initially developed using bone marrow cells from B6D2F$_1$ mice. To determine if hematopoiesis could be supported from other mouse strains a variety of different strains (obtained from Charles River Laboratories) commonly used by researchers, were used to establish long-term bone marrow cultures. The cultures were set up as previously described by flushing the femoral bone marrow into IMDM, washing the cells 3 times and then adding them to IMDM and the serum-free ingredients (including hydrocortisone). The cell suspension is then put into wells pre-coated with collagen and fibronectin and incubated for 3 weeks, with bi-weekly replacement of half the medium after the first week. After this period of time the number of non-adherent cells produced 4 days after the last feed were counted.

Figure 7:
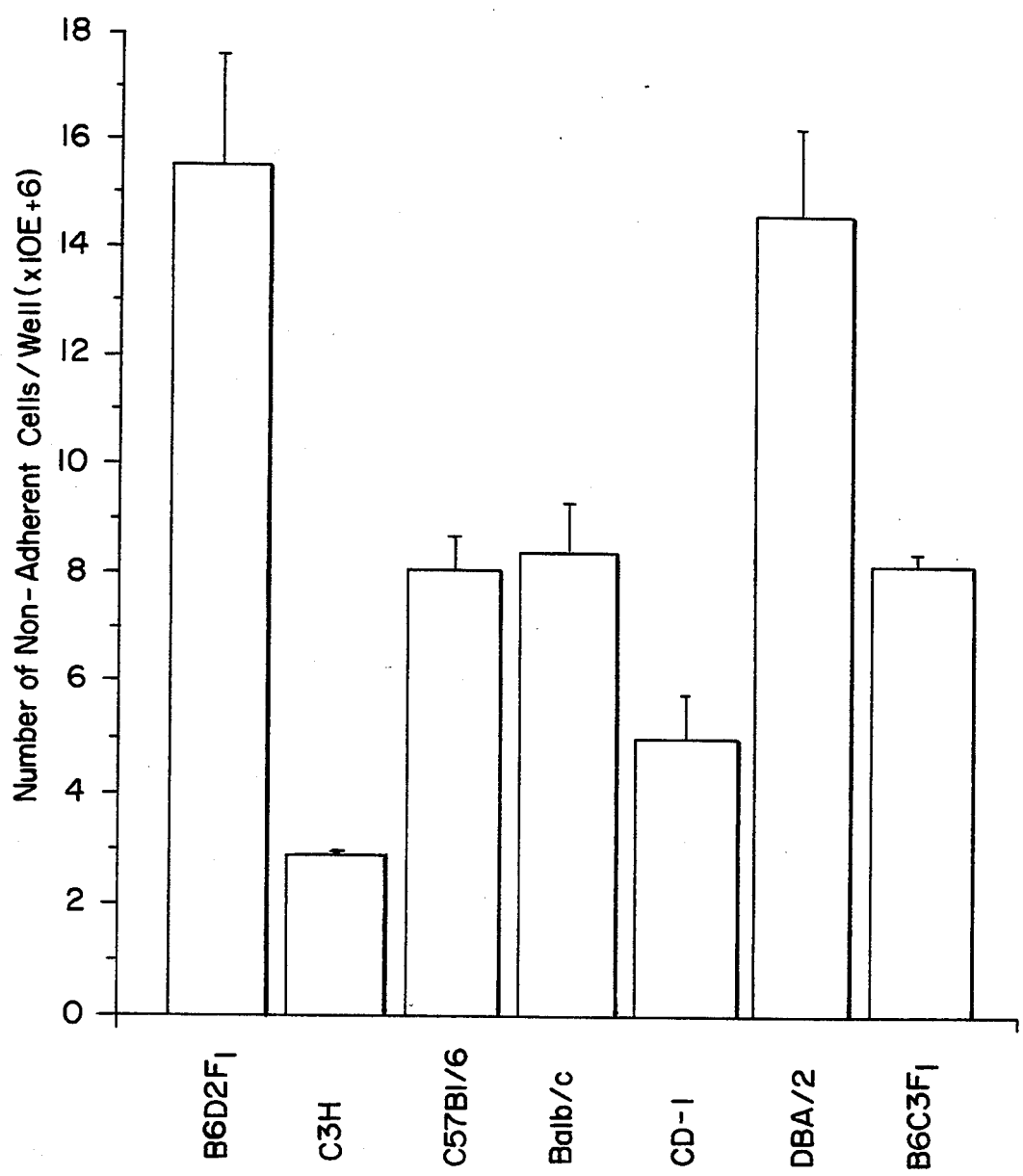
FIG. 7 depicts the production of non-adherent hematopoietic cells after 21 days from serum-free long-term bone marrow cultures when using different strains of mice. C3H, C57Bl/6, Balb/c, and DBA/2 are inbred strains of mice; CD-1 is an outbred strain of mouse; while B6D2F$_1$ (BDF1) and B6C3F$_1$ are hybrids (female C57Bl/6×male DBA/2 and female C57Bl/6×male C3H respectively). Error bars show standard errors.

FIG. 7 shows that the serum-free medium supported hematopoiesis from all strains of mice tested, whether they were inbred, outbred or hybrid mice. B6D2F$_1$ and DBA/2 produced the greatest level of hematopoietic cell production, the cells mainly being neutrophils and macrophageso Visually it was observed that the wells were full of non-adherent cells. The C57Bl/6, Balb/c and B6C3F$_1$ strains produced approximately 50% of the number of hematopoietic cells produced by these two strains. The strains CD-1 and C3H produced the least number of cells but the production in these cultures increased, reaching a maximum after 4–5 weeks, rather than after 3 weeks as for the other strains. Hematopoiesis has been successfully established from other strains of mice, such as B6C3Fe-a/a-op/op, and it is likely that the same will be true for all mouse strains.

Example 6

Lymphocyte containing long-term bone marrow cultures

The hematopoietic development which occurs in the serum-free long-term bone marrow cultures described in the examples so far is primarily neutrophilic and monocyte/macrophage, similar to that which occurs in serum supplemented Dexter cultures. However in the bone marrow in vivo other types of hematopoietic cells are produced including B lymphocytes, megakaryocytes and erythrocytes. It was determined that removing hydrocortisone which is toxic and/or inhibitory for the development of these cells in our long-term bone marrow cultures resulted in a greater probability of these cells occurring. This could be increased even further in the absence of the growth factor CSF-1 (M-CSF) which is normally present at high concentrations in these cultures and is possibly acting as a dominant growth and developmental stimulus, so that macrophage and neutrophil development is more likely to occur than other types of development. The removal of CSF-1 was achieved using a mutant mouse strain the B6C3Fe-a/a-op, which in the homozygous state does not produce any CSF-1 due to a point mutation resulting in the absence of mRNA production for this protein. This lack of CSF-1 has a number of effects on the animals including the absence of the front incisors early in life, malformation of bones caused by a reduced number of osteoclasts, a profound decrease in the number of macrophages and infertility.

The cultures were established using the standard procedures already described in detail. The $B6C3F_1$ mice were obtained from Jackson Laboratories and the femurs and tibias used 2–4 weeks after birth. The bones were ground up using a pestle and mortar and the cells washed 3 times, the single cell suspension obtained was then added to IMDM and the serum-free medium ingredients (no hydrocortisone was added) in the extracellular matrix (collagen IV and fibronectin) pre-coated wells. The cultures were then incubated for 3 weeks, with bi-weekly feeding after the first week, after which time the morphology of the cells was determined.

FIG. 8 shows that in the $B6C3F_1$-a/a-+/+ cultures stimulated with hydrocortisone the majority of the non-adherent cells produced are neutrophils. There are also significant numbers of macrophages produced in these cultures but the majority remain adhered to the surface of the well. In contrast those normal cultures not stimulated with hydrocortisone produce a much smaller number of total non-adherent cells which are all macrophages. The likely explanation for these differences is that hydrocortisone is either having a direct effect on the development of primitive progenitor cells or is having an indirect effect by stimulating growth factor receptor expression on cells and/or production of growth factors which stimulate neutrophil development such as G-CSF and GM-CSF. However, in the absence of hydrocortisone the main developmental stimulus will be CSF-1, a factor which stimulates macrophage development and is produced endogenously in these cultures at comparatively high concentrations. Therefore, the cell development will be skewed in favor of monocytes and macrophages.

$B6C3F_1$-a/a-op/op cultures stimulated with hydrocortisone produce a similar large number of neutrophils as observed with normal +/+ cultures (data not shown). However, in the absence of hydrocortisone the development is different. The most noticeable change is that B lymphocytes are now present in significant numbers (approximately 17%) as shown by morphology and immunocytochemical staining using the B220 antigen and surface immunoglobulin (sIgM). Neutrophils are still numerically the main cell type produced, representing 80% of the cells, with small numbers (3%) of mast cells also being observed.

The presence of B lymphocytes in these cultures clearly requires the absence of hydrocortisone and CSF-1, the hydrocortisone being toxic for lymphocytes and CSF-1 probably acting as a dominant developmental factor, so that macrophage development is stimulated rather than that of B cells. The removal of CSF-1 and therefore macrophages obviously enables the development of cells which would not otherwise be observed, and enables greater control over the culture, since the dominant effect of CSF-1 no longer has to be overcome. An example of this is shown in FIG. 8 where stem cell factor (SCF) and IL-7 are added to OP/OP cells without hydrocortisone. In these cultures there is an increase in the relative number of B cells and mast cells, IL-7 stimulating B cell proliferation and SCF stimulating mast cell proliferation.

Example 7

Establishment of Serum-Free Cultures from Mouse or Human Organs and Tissues.

Serum-free long-term bone marrow cultures can be established from a wide variety of different organs such as spleen, fetal liver, heart, lung, kidney, liver and brain. A single cell suspension is first prepared by cutting the organs into small pieces. Certain organs such as the spleen, brain and fetal liver are easily disaggregated so these are put straight into a tissue homogenizer. In contrast the lung, liver, kidney and heart are more difficult to disaggregate so they are treated with 2 mg/ml collagenase (Sigma) dissolved in IMDM and 20 mg/ml bovine serum albumin (Sigma), at 37° C. for 1.5 hr to digest the tissue prior to homogenizing. The cell suspension obtained is then allowed to settle for a few minutes so that the tissue debris can be removed and discarded. This single cell suspension is then washed three times by centrifuging the cells and then resuspending them in a 10 ml volume, this process is repeated twice and the cells resuspended at a suitable concentration ready for use.

After preparation, 1 ml of this cell suspension is then added to 1.22 ml of fresh or frozen concentrated serum-free medium (not containing hydrocortisone unless culturing spleen or fetal liver where hematopoiesis is required) and IMDM (supplemented with glutamine, penicillin and streptomycin as usual), in 6 well trays (Falcon) precoated with collagen IV and fibronectin. The initial cell density in these cultures will vary depending on the type of cell used; fetal liver cultures are established at $10^6$–$5 \times 10^6$/well, spleen cultures at $5 \times 10^6$–$5 \times 10^7$/well, and other organs at $5 \times 10^6$–$10^7$/well. The cells are then incubated at 37° C. in a humidified incubator containing 5% $CO_2$ in air, with weekly feeding where half of the medium is removed and replaced with fresh.

Cultures set up in this way enable hematopoiesis to occur from spleen and fetal liver cells. In addition, all the different organs produce a confluent layer of heterogeneous cells (as determined by morphology and staining for the presence of various enzymes such as alkaline and acid phosphatase) which are native to the organ cultured.

What is claimed as new and desired to be protected by Letters Patent of the United States is:

1. A medium for the long-term proliferation and development of cells, which comprises the following ingredients in the indicated amounts:

| | | |
|---|---|---|
| (a) | a standard culture medium | 0.8–1.09 x, |
| (b) | serum albumin | 3–50 mg/ml, |
| (c) | transferrin | 25–1000 ug/ml, |
| (d) | lipids and fatty acids | 5–100 ug/ml, |
| (e) | cholesterol | 3–30 ug/ml, |
| (f) | reducing agent | 30–300 uM, |
| (g) | pyruvate | 30–500 ug/ml, |
| (h) | nucleosides | 5–30 ug/ml, |

(i) at least one growth factor selected from the group consisting of:

| | |
|---|---|
| (1) epidermal growth factor | 5–200 ng/ml |
| (2) fibroblast growth factor | 0.5–40 ng/ml |
| (3) platelet-derived growth factor | 2–200 ng/ml; and |
| (4) insulin | 2–100 ug/ml. |

(j) at least one extracellular matrix material selected from the group consisting of:

| | |
|---|---|
| (1) collagen IV | 2–100 ug/cm$^2$; and |
| (2) fibronectin | 0.5–100 ug/cm$^2$; | wherein said medium for the long-term proliferation and development of cells is serum-free or serum-depleted and is capable of culturing cells comprising adipocytes, macrophages, endothelial cells, fibroblasts, and hematopoictic progenitor cells.

2. The medium according to claim 1, further comprising a glucocorticoid.

3. The medium according to claim 1, wherein said glucocorticoid is hydrocortisone.

4. The medium according to claim 1, further comprising stromal cells.

5. The medium according to claim 1, further comprising an inhibitor of CSF-1 activity.

6. The medium according to claim 1, wherein said cells to be cultured are incapable of producing CSF-1.

7. The medium according to claim 6, wherein said cells to be cultured are obtained from a B6C3Fe-a/a-op/op mouse strain.

8. The medium according to claim 1, wherein said standard culture medium is Iscove's Modified Dulbecco's Medium.

9. The medium according to claim 1, wherein said serum albumin, transferrin and growth factors are each of human, mouse or bovine origin.

10. The medium according to claim 1, wherein said nucleosides are one or more selected from the group consisting of adenosine, guanosine, cytidine, uridine, 2'-deoxyadenosine, 2'-deoxyguanosine, 2'-deoxycytidine and thymidine.

11. The medium according to claim 1, wherein all of said extracellular matrix materials are included.

12. The medium according to claim 1, wherein said cells are hematopoietic or lymphopoietic.

13. The medium according to claim 1, wherein said cells are from mammalian organs or tissues.

14. The medium according to claim 1, wherein said cells are primary cells or cell lines.

15. A method of long-term culture of cells which comprises culturing the cells for 8 to 20 weeks in the medium according to claim 1.

16. A method of short-term culture of cells which comprises culturing the cells for 2 to 7 weeks in the medium according to claim 1.

* * * * *